United States Patent
Weinstein

[11] Patent Number: 5,848,976
[45] Date of Patent: Dec. 15, 1998

[54] ALLERGIC RHINITIS RELIEF SYSTEM AND PROCESS

[76] Inventor: Robert E. Weinstein, 177 Commonwealth Ave., Boston, Mass. 02116

[21] Appl. No.: 801,259

[22] Filed: Feb. 19, 1997

[51] Int. Cl.$^6$ ........................................ A61B 5/00
[52] U.S. Cl. ........................................ 600/556
[58] Field of Search .................. 600/551, 556, 600/587; 206/569, 570

[56] References Cited

U.S. PATENT DOCUMENTS 4,295,567  10/1981  Knudsen .
5,099,857   3/1992  Baldo et al. .............................. 600/556

FOREIGN PATENT DOCUMENTS 5253191  10/1993  Japan ...................................... 600/556

OTHER PUBLICATIONS

R. Michael Sly, Principles of Diagnosis and Treatment of Allergic Diseases, in Allergic Diseases from Infancy to Adulthood, 217–219 (C. Warren Bierman and David S. Pearlman eds., 2d ed. 1988).

David G. Tinkelman, Principles of Diagnosis and Management, in Allergy, Asthma, and Immunology from Infancy to Adulthood, 135–137 (C. Warren Bierman et al. eds., 3d ed. 1996).

Fuad M. Baroody and Robert M. Naclerio, Allergic Rhinitis, in Clinical Immunology Principles and Practice, 889–908 (Robert R. Rich et al. eds, 1996).

Primary Examiner—Max Hindenburg
Attorney, Agent, or Firm—Morse & Altman

[57] ABSTRACT

An allergy treatment that combines graphical indicia and medicinal dosages in at least three logically related physical formats, according to at least three medically related clinical steps. The first physical format, in reference to Step 1, presents a plurality of categories of queries regarding allergenic substances and conditions. The second physical format, in reference to Step 2, presents a plurality of categories of actions regarding recommendations for allergy avoidance. The third physical format, in reference to Step 3, presents one or more categories of medicinal dosages in one or more logically related physical regions, which are accompanied by a set of instructions. The arrangement is a program of artificial intelligence in which the patient is enabled by medical expertise: to select pertinent allergenic factors which are defined by the queries presented in Step 1; to select pertinent salutary recommendations which are defined by the actions presented in Step 2; and to implement or avoid the medicinal regimen that is provided and defined by the modules and indicia presented in Step 3. The steps together provide interrelated records for current and future evaluation.

22 Claims, 13 Drawing Sheets

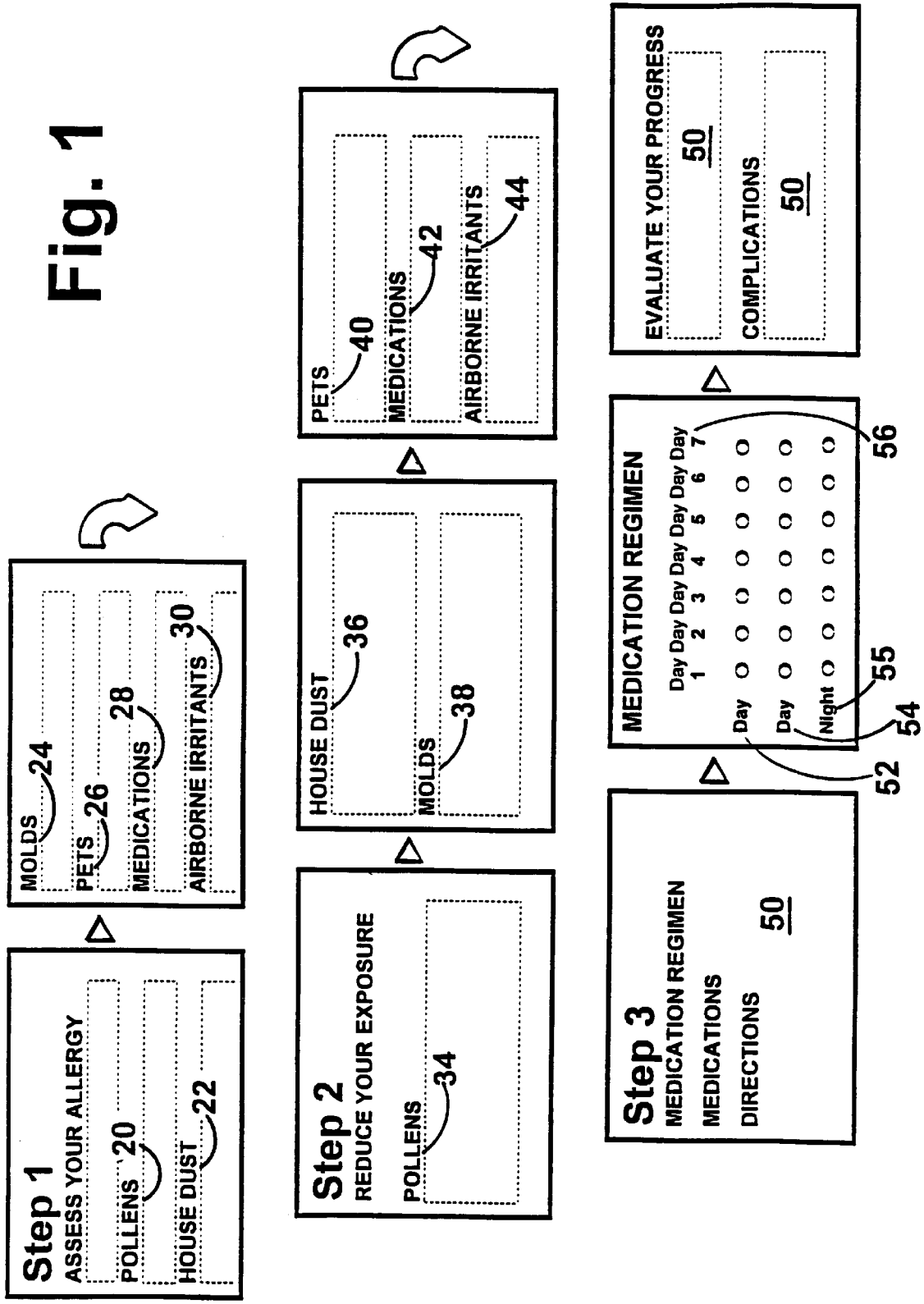

Step 1
YOUR ALLERGY ASSESSMENT

POLLENS, HOUSE DUST, MOLDS and PETS are the most common causes of allergies!

If Applicable:

POLLENS tend to cause allergies in the spring, summer and fall! Are you worse in:
- ☐ The early spring (when trees pollinate)?
- ☐ May-June (when grass pollinates)?
- ☐ August-September (when fall weeds and ragweed pollinate)? —33

HOUSE DUST causes allergy symptoms throughout the year--especially during the colder months when the house is more closed! Some individuals have dust allergies throughout the year and become worse during pollen season!
- ☐ Do you get worse in dusty environment? —33
- ☐ Is your home or work setting dusty?
- ☐ Is your mattress more than 10 years old?
- ☐ Are you using feather pillows or comforters?
- ☐ Do you have old or dusty stuffed furniture?
- ☐ If you have forced air heat, do you allow the air filters to get old or dusty?

Fig. 2a

24 — MOLDS grow in warm, damp environments. Suspect molds with damp weather symptoms, which do not coincide with a pollen season!

32 —
- ☐ Do you get worse in damp weather or damp environments? 33
- ☐ Does your home have a damp basement?
- ☐ Are other areas in your home damp or musty?
- ☐ Is your environment at work damp or musty?
- ☐ Is your home filled with plants?

26 — PETS can cause symptoms throughout the year!
- ☐ Do your allergy symptoms get worse near animals? 33
- ☐ Do you have dogs, cats, hamsters, rabbits or other pets?
- ☐ Does you dog or cat have the run of the house?

28 — MEDICATIONS can sometimes cause or worsen nasal symptoms! Are you taking any of the following?
- ☐ Decongestant nose spray? 33
- ☐ Blood pressure medication?
- ☐ Aspirin or other anti-inflammatory medication?
- ☐ Female hormones?

30 — AIRBORNE IRRITANTS aggravate allergies and also cause symptoms in individuals who do not have allergies but have sensitive noses! Are you ever bothered by? 33
- ☐ Aerosols       ☐ Perfumes and strong odors
- ☐ Newspaper ink  ☐ Tobacco smoke

Fig. 2b

Step 2

DECREASE YOUR ALLERGY EXPOSURE

The best treatment for allergies is to avoid the cause! Pay special attention to the causes of allergy that you checked in Step 1 and follow the following recommendations!

POLLENS

- Limit your outdoor exposure during the season when you are having symptoms!

- Avoid outdoor activity in the early morning and evening hours when pollen counts are highest!

- Keep your windows closed at home and at work, and use air conditioning, if available, on "circulate," not "ventilate" mode to eliminate bringing pollen indoors!

- Drive your automobile with the windows closed!

- Avoid cutting the grass, especially during May and June!

- You may find a room air filter helpfull If possible, try before buying!

Fig. 3a

HOUSE DUST

- Avoid feather pillows and old cotton pillows! A synthetic pillow is suggested!
- Replace old mattresses or use a plastic cover and new pad to enclose them!
- Avoid feather quilts and old stuffed quilts which may become dusty! Washable blankets are suggested!
- Use hot water when washing linens and blankets! (This helps eliminate house dust mites, an important sensitizer in dust.)
- Avoid or remove old stuffed furniture, rugs and other dust collectors!
- Replace furnace filters and air conditioner filters frequently!
- Consider room air filters or a central air filter to help decrease dust!

MOLDS

- Avoid prolonged exposure to damp and musty environments!
- Keep your basement dry by ventilating or using a dehumidifier!
- Correct structural problems, which may be creating mildew or moisture at home or work!
- Avoid creating excess moisture by overusing humidifiers during the colder months!
- Limit the number of indoor plants!

Fig. 3b

PETS
- Notice if you are better away from your pet, possibly when you are away from home!
- If your pet has the run of the house, experiment with keeping the pet out of the bedroom, or in a limited area of the house to minimize exposure to dander (skin scales) and saliva which can cause symptoms!
- Washing your pet frequently may decrease the amount of dander it sheds!
- Consider boarding the pet with a veterinarian or friend to determine how you are with the pet away for a period of time!

MEDICATIONS
- Avoid prolonged use of over-the-counter decongestant nose drops and sprays, which can cause irritation and added nasal congestion!
- Consult with your physician if you are taking high blood pressure medicine, or suspect that symptoms are worsening with female hormones, aspirin or other anti-inflammatory medications!

AIRBORNE IRRITANTS
- Avoid tobacco smoke, perfumes, and other irritants, which may increase your symptoms!

Allergy avoidance can be sufficient to bring about relief, especially if you are able to completely avoid the cause. If you are being as careful as you can, and still suffer from allergy, proceed to Step 3!

Fig. 3c

Step 3
MEDICATION REGIMEN

MEDICATIONS
Coordinate your need for medication with Step 1 and Step 2. This care path contains two immediate acting medications, a White Decongestant Tablet for daytime, which is non-drowsy, and a Yellow Antihistamine Tablet for nighttime, which allows rest.

DIRECTIONS
<u>Adults and children 12 years of age and over:</u>
Daytime: Take 1 White Decongestant Tablet in the morning as needed. Repeat 6 hours later in the afternoon as needed.
Nighttime: Take 1 Yellow antihistamine Tablet in the morning as needed.
<u>Children 6 to 11 years of age:</u> One half of the adult dose (break tablet in half).
Some adults may find that ½ the adult dose (½ tablet) will be effective rather than 1 tablet.

CAUTIONS
- Do not exceed the recommended dosage.
- The Daytime White Decongestant Tablet may cause insomnia if taken at night.
- The Nighttime Antihistamine Tablet may cause drowsiness if taken during the day.
- Consult with your physician if you have elevated blood pressure, heart disease, glaucoma, thyroid disorder, seizure disorder, difficulty in urination due to enlargement of the prostate gland, diabetes, or are taking medications for depression, emotional conditions or Parkinson's Disease.

EVALUATE YOUR PROGRESS

If you are like most people, these three steps will help you to control your symptoms. Evaluate your progress to determine if you are sufficiently improved or if additional medical attention is required.

COMPLICATIONS

Common allergy symptoms include: stuffy nose, runny nose, sneezing, watery eyes, itchy eyes, sinus fullness, fatigue, irritability, post-nasal drip and cough. If you experience any of the following symptoms, it is recommended that you notify your physician:

Severe fullness or pain above the eyes or in the area of the cheekbones with headache fever or yellow nasal discharge!

Loss of sense of smell!

Ear pain or loss of hearing!

Severe or persistent sore throat!

Excessive cough, or chest congestion, chest pain, shortness of breath or wheezing!

Persistent fever, rash or joint tenderness!

If you require a doctor's visit, bring your care path record with you.

MEDICATION INDICATIONS AND WARNINGS    50

Daytime White DecongestantTablet
Indications: For the temporary relief of nasal congestion due to the common cold, hay fever or other respiratory Allergies; promotes nasal and/or sinus drainage; temporarily relieves sinus congestion and pressure.
Active ingredients: Each tablet contains 60 mg pseudoephedrine hydrochloride.
Warnings: Do not exceed recommended dosage. If nervousness, dizziness, or sleeplessness occur discontinue use and consult a doctor. If symptoms do not improve within 7 days or are accompanied by a fever, consult a doctor. Do not take this meditation if you have heart disease, high blood pressure, thyroid disease, diabetes, or difficulty in urination due to enlargement of the prostate gland unless directed by a doctor.
Drug interaction precaution: Do not use this product if you am now taking a prescription monoamine oxidase inhibitor (MAOI) (certain drugs for depression, psychiatric or emotional conditions, or Parkinson's Disease), or for 2 weeks after stopping the MAOI drug. If you are uncertain whether your prescription contains an HAOI, consult a health care professional before taking this product,

Nighttime Yellow Antihistamine Tablet:
Indications: for the temporary relief of runny nose, sneezing, itching of the nose, watery eyes due to hay fever or other upper respiratory allergies.
Active Ingredient: Each tablet contains 4mg Chlorpheniramine Maleate.
Warnings: May cause excitability especially in children. Do not tale this product unless directed by a doctor, if you have a breathing problem such as emphysema or chronic bronchitis, or if you have glaucoma or difficulty in urination due to enlargement of the prostate gland. Hay cause drowsiness: alcohol, sedatives, and tranquilizers may increase the drowsiness effect, Avoid alcoholic beverages while taking this product. Do not take this product if you are taking sedatives or tranquilizers, without first consulting your doctor. Use caution when driving a motor vehicle or operating machinery.

As with any drug, if you are pregnant or nursing a baby, seek the advice of a health care professional before using these meditations. Keep this and all medicines out of the reach of children. In case of accidental overdose, seek professional assistance or contact a Poison Control Center immediately. Store between 59° and 86°F (15° to 30°C). Protect from excessive moisture and light.

Fig. 4d

Step 2

DECREASE YOUR ALLERGY EXPOSURE

The best treatment for allergies is to avoid the cause! Pay special attention to the causes of allergy that you checked in Step 1 and follow the following recommendations!

POLLENS
- ☐ Limit your outdoor exposure during the season when you are having symptoms!
- ☐ Avoid outdoor activity in the early morning and evening hours when pollen counts are highest!
- ☐ Keep your windows closed at home and at work, and use air conditioning, if available, on "circulate," not "ventilate" mode to eliminate bringing pollen indoors!
- ☐ Drive your automobile with the windows closed!
- ☐ Avoid cutting the grass, especially during May and June!
- ☐ You may find a room air filter helpful! If possible, try before buying!

Fig. 5a

HOUSE DUST

- Avoid feather pillows and old cotton pillows! A synthetic pillow is suggested!
- Replace old mattresses or use a plastic cover and new pad to enclose them!
- Avoid feather quilts and old stuffed quilts which may become dusty! Washable blankets are suggested!
- Use hot water when washing linens and blankets! (This helps eliminate house dust mites, an important sensitizer in dust.)
- Avoid or remove old stuffed furniture, rugs and other dust collectors!
- Replace furnace filters and air conditioner filters frequently!
- Consider room air filters or a central air filter to help decrease dust!

MOLDS

- Avoid prolonged exposure to damp and musty environments!
- Keep your basement dry by ventilating or using a dehumidifier!
- Correct structural problems, which may be creating mildew or moisture at home or work!
- Avoid creating excess moisture by overusing humidifiers during the colder months!
- Limit the number of indoor plants!

Fig. 5b

PETS

☐ Notice if you are better away from your pet, possibly when you are away from home!

☐ If your pet has the run of the house, experiment with keeping the pet out of the bedroom, or in a limited area of the house to minimize exposure to dander (skin scales) and saliva which can cause symptoms!

☐ Washing your pet frequently may decrease the amount of dander it sheds!

☐ Consider boarding the pet with a veterinarian or friend to determine how you are with the pet away for a period of time!

MEDICATIONS

☐ Avoid prolonged use of over-the-counter decongestant nose drops and sprays, which can cause irritation and added nasal congestion!

☐ Consult with your physician if you are taking high blood pressure medicine, or suspect that symptoms are worsening with female hormones, aspirin or other anti-inflammatory medications!

AIRBORNE IRRITANTS

☐ Avoid tobacco smoke, perfumes, and other irritants, which may increase your symptoms!

Allergy avoidance can be sufficient to bring about relief, especially if you are able to completely avoid the cause. If you are being as careful as you can, and still suffer from allergy, proceed to Step 3!

Fig. 5c

ALLERGIC RHINITIS RELIEF SYSTEM AND PROCESS

BACKGROUND OF THE INVENTION

1. Field of the Invention

Allergic rhinitis is a chronic medical ailment that afflicts millions of people throughout the industrialized world. Common allergenic substances and conditions are universally prevalent in permutations and combinations that confuse both patients and doctors, that inhibit insight into etiology, that limit doctor-patient communication, that restrict accurate feedback and interpretation of clinical results, and that impair diagnosis and therapy.

2. The Prior Art

A variety of helpful medications now are available, by prescription and over-the-counter, for treating allergic rhinitis. Difficulties have been encountered in systematically prescribing, adapting, monitoring, recording, and adjusting the selection and application of available medications. Allergy avoidance should be the initial focus of any strategy for treating allergic rhinitis, and should be practiced concomitantly with other treatments. Lack of a consistent program for implementing a sound strategy often has resulted in unnecessary use of costly medication and medical services. Prior strategies often have ignored inquiry into environmental factors in a manner that has been insufficiently oriented toward patient self-help and that has caused undue dependence on attention by medical personnel.

SUMMARY OF THE INVENTION

The present invention relates to systems and processes for the treatment of allergic rhinitis, and, more particularly, to practical systems and processes for ameliorating the treatment of allergic rhinitis by reducing inherent confusion, encouraging effective patient self-help, improving and expediting medical evaluation and enhancing doctor-patient communication.

Specifically, the system and process of the present invention contemplate combining graphical indicia and medicinal dosages in at least three logically related physical formats, according to at least three medically related clinical steps. The first physical format, in reference to Step 1, presents a plurality of categories of queries regarding allergenic substances and conditions. The second physical format, in reference to Step 2, presents a plurality of categories of actions regarding recommendations for allergy avoidance. The third physical format, in reference to Step 3, presents one or more categories of medicinal dosages in one or more logically related physical regions, which are accompanied by a set of instructions. Preferably, the third physical format includes sequences of modules that are defined in at least one blister-pack array that includes a formed plastic sheet with pockets for receiving the dosages and a rupturable aluminum cover for retaining the dosages in their modules until removed manually.

Each of the categories in Step 1 is designated by a medical identifier that is unique within Step 1. Each of the categories in Step 2 is designated by a medical identifier that is unique within Step 2. Each medical identifier in Step 1 is substantially identical to a corresponding medical identifier in Step 2 and vice versa. The modules of any sequence in Step 3 are in proximity to indicia that designate increments of time. The arrangement is a program of artificial intelligence in which the patient is enabled by medical expertise: to select pertinent allergenic factors which are defined by the queries presented in Step 1; to select pertinent salutary recommendations which are defined by the actions presented in Step 2; and to implement or avoid the medicinal regimen that is provided and defined by the modules and indicia presented in Step 3. The steps together provide interrelated records for current and future evaluation.

The present invention improves patient understanding of allergy causation and treatment strategies, suggests an environmental allergy control plan to the patient, enhances the patient-doctor and care path partnership, improves clinical outcomes, and reduces costs for allergy care.

BRIEF DESCRIPTION OF THE DRAWINGS

For a fuller understanding of the nature and objects of the present invention, reference is made to the following specification, which is to be taken in connection with the accompanying drawings, wherein:

FIG. 1 is a flow diagram illustrating the three formats of the system and the three steps of the process of the present invention.

FIGS. 2a and 2b illustrate an example of a printed format for allergy assessment that corresponds to Step 1.

FIGS. 3a, 3b and 3c illustrate an example of a printed format for allergy exposure recommendations that corresponds to Step 2.

FIGS. 4a, 4b, 4c and 4d illustrate an example of a blister pack and printed format for carrying sequences of medicinal dosages, identifying the timing of successive dosages, and providing background medical information.

FIGS. 5a, 5b and 5c illustrate another example of a printed format for allergy exposure recommendations that corresponds to Step 2.

DETAILED DESCRIPTION OF THE PREFERRED EMBODIMENT

Figure 4B:
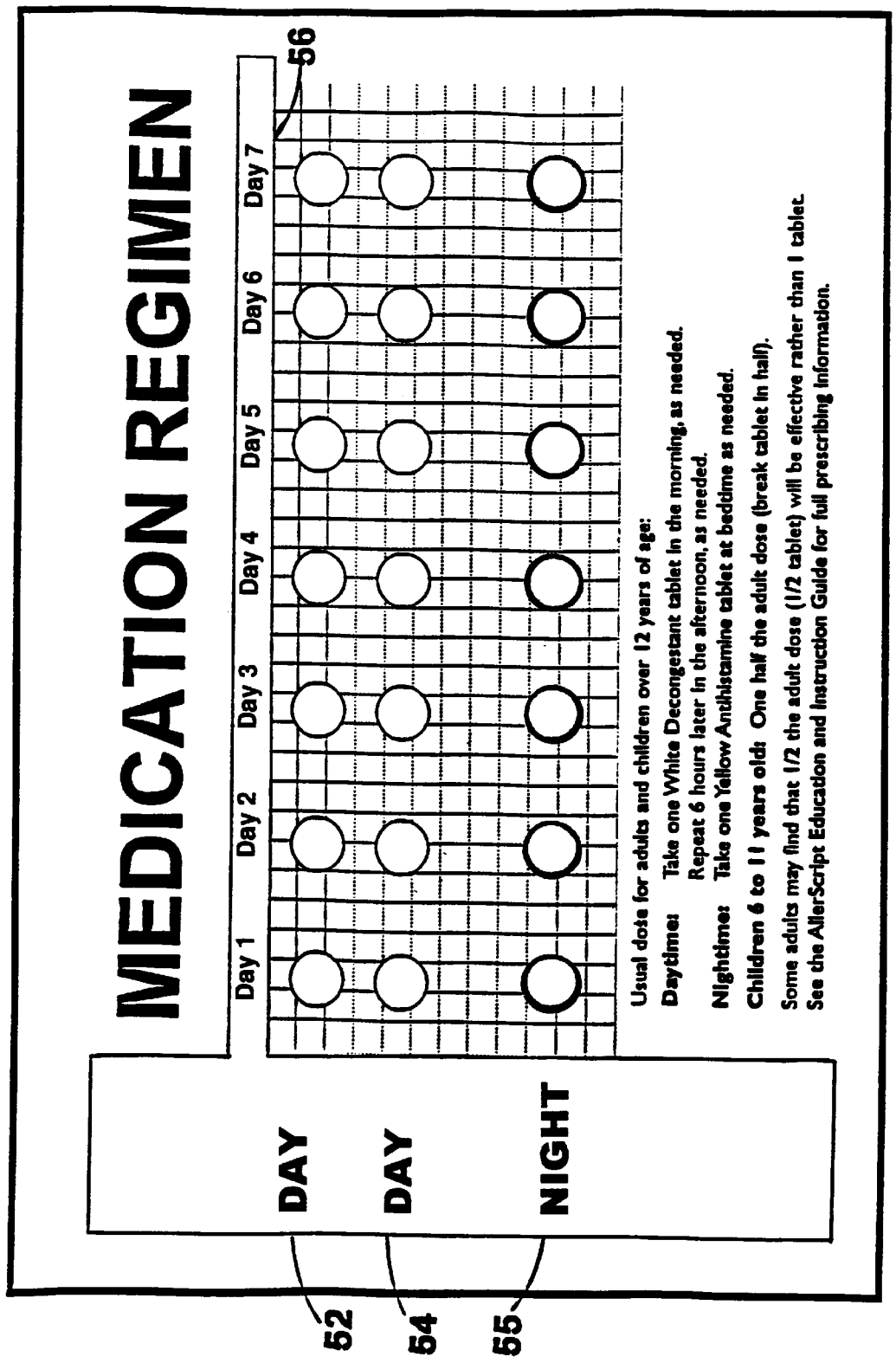

This allergy relief program, in effect, implements a cost-effective model, which standardizes delivery of care for allergic rhinitis. In its preferred embodiment, it includes a plan having three steps. Step 1 provides a record that interactively effects an Allergy Assessment. Step 2 provides a record that effects recommendations for Allergy Exposure Reduction as a function of Step 1. And Step 3 provides at least one sequential array of dosage units, which effect a Medication Regimen that is timed as a function of Steps 1 and 2. After completion, the allergy relief system and process of the present invention provide a permanent record to support current and future treatment.

The allergy relief program of the present invention may be particularly useful within health maintenance organizations (HMO's) and managed care plans, and may be utilized in the context of care criteria for specific patient populations or medical practice patterns. Suggested criteria for inclusion in the care path are stuffy nose, runny nose and sneezing, which may be associated with eye watering and itching, post-nasal drip and sinus fullness. Suggested criteria for exclusion from the care path of the present invention, indicative of infection or other complications, are pain in the sinus areas with fever, ear pain or loss of hearing, loss of sense of smell, severe or persistent sore throat, wheezing, shortness of breath, fever, and rash or joint tenderness. Patients who do not meet the care criteria of the present invention may be directed to their attending physician. Patients with heart disease, high blood pressure, thyroid disease, diabetes, seizure disorders, difficulty in urination due to enlargement of the prostate gland or taking monoamine oxidase (MAO) inhibitors also may require direction by their physicians. After resolution of such complications, patients become eligible to proceed with use of the present invention.

As shown in FIG. 1, the illustrated embodiment physically implements the three steps of the present invention in a combination of graphical indicia and medicinal dosages in at least three logically related physical formats. The first physical format, in reference to Step 1, includes a record containing references to a plurality of categories of allergenic substances and conditions. The second physical format, in reference to Step 2, includes a record containing references to a plurality of categories of recommendations. The third physical format, in reference to Step 3, includes one or more categories of medicinal dosages in one or more logically related physical regions. These dosages, which are accompanied by a set of instructions, are distributed in sequences of modules that are defined in a blister-pack array that includes a formed plastic sheet with pockets for receiving the dosages and a rupturable aluminum cover for retaining the dosages in their modules until removed manually.

As shown in FIGS. 1, 2a and 2b, the first physical format, in reference to Step 1, includes a record that refers to a plurality of categories of interactive base line queries. Each of the categories in Step 1 is designated by a query identifier that is unique within Step 1. Specifically, these query identifiers include POLLENS 20, HOUSE DUST 22, MOLDS 24, PETS 26, MEDICATIONS 28, and AIRBORNE IRRITANTS 30. Each of the categories specified by these query identifiers is followed by a series of queries that are associated with check boxes 32, by which a patient is guided to specify applicable allergenic factors. Each of these queries is followed by a question mark 33.

As shown in FIGS. 1, 3a, 3b and 3c, the second physical format, in reference to Step 2, includes a record that refers to a plurality of categories of responsively recommended actions. Each of the categories in Step 2 is designated by a action identifier that is unique within Step 2. Specifically, these action identifiers include POLLENS 34, HOUSE DUST 36, MOLDS 38, PETS 40, MEDICATIONS 42, and AIRBORNE IRRITANTS 44. Each of the categories specified by these action identifiers is followed by a series of suggested actions that are associated with bullet points 46, by which a patient is guided to take appropriate preventative measures. Each of these actions is followed by an exclamation mark 48.

As shown in FIGS. 1, 4a, 4b and 4c, the third physical format, in reference to Step 3, includes applicable medical information 50, and groups of medicinal dosages in logically related physical regions 52, 54, 55. These dosages are distributed in sequences of modules that are defined in a blister-pack array that includes a formed plastic sheet with pockets for receiving the dosages and a rupturable aluminum cover for retaining the dosages in their modules until removed manually. In the illustrated embodiment, the modules of any sequence in Step 3 are in proximity to indicia 56 that designate increments of time, which establish a time line that is related to the aforementioned query and action identifiers.

In one embodiment, the illustrated allergy relief system contains two blister packs of the type shown in FIGS. 1 and 4b, by which it is adapted for a package, which contains a 14-day medication regimen with pseudoephedrine for day and chlorpheniramine for night. These single entity medications are well characterized and have had long and widespread use. The concept of exploiting the characteristics of separate entities for day and night dosing is disclosed in U.S. Pat. No. 4,295,567. Removing dosages from their modules, after establishing a base line pursuant to Step 1 and following the recommendations of Step 2, inherently optimizes the medicinal regimen of Step 3 and produces a permanent record as a basis for further treatment. Therapeutic benefit is optimized and side effects minimized by this novel dosing regimen.

Another embodiment of the present invention includes an alternative Step 2, which is shown in FIGS. 5a, 5b and 5c. In this embodiment, the second physical format, in reference to Step 2, includes a record that refers to a plurality of categories of responsively recommended actions. Each of the categories in Step 2 is designated by an action identifier that is unique within Step 2. Specifically, these action identifiers include POLLENS 60, HOUSE DUST 62, MOLDS 68, PETS 70, MEDICATIONS 72, and AIRBORNE IRRITANTS 74. Each of the categories specified by these action identifiers is followed by a series of suggested actions that are associated with check boxes 62, by which a patient is guided to take appropriate preventative measures. Each of these actions is followed by an exclamation mark 64.

The medicinal dosages in reference to Step 3 are shown in a blister pack format in the preferred embodiment. However, the present invention contemplates alternative dosage formats, such as liquids, powders, capsules, etc., accompanied by logically related indicia and instructions, which coordinate their use in conjunction with Steps 1 and 2.

OPERATION

It will be observed that each query identifier in Step 1 is substantially identical to a corresponding action identifier in Step 2 and vice versa. It will be observed also that all of the sections of the sections of the illustrated physical formats as shown in the drawings are of identical size and shape. This identity of format visually aids in comprehending and following the procedures of the present invention. Thus the queries of Step 1 identify relevant allergenic substances and conditions, the recommendations of Step 2 identify relevant needed actions, and the medication regimen of Step 3 provide comprehensive coordinated management of allergic disorders. Removing dosages from their modules pursuant to selected medical identifiers inherently establishes a time line that is related to the aforementioned medical identifiers. The steps together constitute current and future guidance pursuant to a regimen of artificial intelligence that serves as an aid to medical service providers, a self-help guide to patients, and a permanent record for future use by both.

What is claimed is:

1. A medical system for the treatment of allergic rhinitis, said medical system comprising:

(a) at least three logically related physical formats, including a first physical format, a second physical format, and a third physical format;

(b) said first physical format presenting a record that includes a plurality of categories of queries in reference to allergenic substances and conditions;

(c) said second physical format presenting a record that includes a plurality of categories of actions in reference to said allergenic substances and conditions;

(d) said third physical format presenting medicinal dosages and indicia in proximity to said modules, said indicia designating values of time;

(e) each of said categories in said first physical format being designated by a medical value that is unique within said first physical format;

(f) each of said categories in said second physical format being designated by a medical value that is unique within said second physical format;

(g) each medical value in said first physical format being substantially identical to a corresponding medical value in said second physical format;

(h) said categories being functionally related to said medicinal dosages and to said values of time;

(i) the medical values of said categories of said first physical format consisting essentially of POLLENS, HOUSE DUST, MOLDS, PETS, MEDICATIONS, and AIRBORNE IRRITANTS;

(j) the medical values of said categories of said second physical format consisting essentially of POLLENS, HOUSE DUST, MOLDS, PETS, MEDICATIONS, and AIRBORNE IRRITANTS, (k) said medicinal dosages incorporating at least a member selected from the class consisting of medicines for alleviating allergic responses to said medical values of said first physical format and said medical values of said second physical format.

2. The medical system of claim 1 wherein the queries within the categories of said first physical format are associated with check boxes.

3. The medical system of claim 1 wherein the queries within the categories of said second physical format are associated with visual attention indicia.

4. The medical system of claim 1 wherein said first physical format, said second physical format and said third physical format, all consist of sections that are substantially of the same size and shape.

5. The medical system of claim 1 wherein each of said queries of said first physical format terminates in a question mark.

6. The medical system of claim 1 wherein each of said actions of said second physical format terminates in an exclamation mark.

7. The medical system of claim 1 wherein said third physical format includes at least two categories of medicinal dosages.

8. The medical system of claim 1 wherein said third physical format includes at least one blister pack of said medical dosages.

9. The medical system of claim 1 wherein said second physical format includes check boxes in close proximity to said actions.

10. A medicinal process for treating allergic rhinitis comprising the steps of:

(a) selecting queries from a first physical format presenting a record that includes a plurality of categories of said queries in reference to allergenic substances and conditions;

(b) selecting actions from a second physical format presenting a record that includes a plurality of categories of actions in reference to said allergic substances and conditions;

(c) optionally selecting medicinal dosages from a third physical format presenting medicinal dosages and indicia in proximity to said modules, said indicia designating values of time;

(d) each of said categories in said first physical format being designated by a medical value that is unique within said first physical format;

(e) each of said categories in said second physical format being designated by a medical value that is unique within said second physical format;

(f) each medical value in said first physical format being substantially identical to a corresponding medical value in said second physical format;

(g) said categories being functionally related to said medicinal dosages and to said values of time;

(h) the medical values of said categories of said first physical format consisting essentially of POLLENS, HOUSE DUST, MOLDS, PETS, MEDICATIONS, and AIRBORNE IRRITANTS;

(i) the medical values of said categories of said second physical format consisting essentially of POLLENS, HOUSE DUST, MOLDS, PETS, MEDICATIONS, and AIRBORNE IRRITANTS;

(k) said medicinal dosages incorporating at least a member selected from the class consisting of medicines for alleviating allergic responses to said medical values of said first physical format and said medical values of said second physical format.

11. The process of claim 10 wherein the queries within the categories of said first physical format are associated with check boxes.

12. The process of claim 10 wherein the queries within the categories of said second physical format are associated with visual attention indicia.

13. The process of claim 10 wherein said first physical format, said second physical format and said third physical format, all consist of sections that are substantially of the same size and shape.

14. The process of claim 10 wherein each of said queries of said first physical format terminates in a question mark.

15. The process of claim 10 wherein each of said actions of said second physical format terminates in an exclamation mark.

16. The process of claim 10 wherein said third physical format includes at least two categories of medicinal dosages.

17. The process of claim 10 wherein said third physical format includes at least one blister pack of said medical dosages.

18. The medical system of claim 10 wherein said second physical format includes check boxes in close proximity to said actions.

19. A medical package for the treatment of allergic rhinitis, said medical package comprising:

(a) at least three logically related physical formats, including a first physical format, a second physical format, and a third physical format;

(b) said first physical format presenting a record that includes a plurality of categories of queries in reference to allergenic substances and conditions;

(c) said second physical format presenting a record that includes a plurality of categories of actions in reference to said allergic substances and conditions;

(d) said third physical format presenting medicinal dosages and indicia in proximity to said medicinal dosages, said indicia designating values of time;

(e) each of said categories in said first physical format being designated by a medical value that is unique within said first physical format;

(f) each of said categories in said second physical format being designated by a medical value that is unique within said second physical format;

(g) each medical value in said first physical format being substantially identical to a corresponding medical value in said second physical format;

(h) said categories being functionally related to said medicinal dosages and to said values of time;

(i) the medical values of said categories of said first physical format consisting essentially of POLLENS, HOUSE DUST, MOLDS, PETS, MEDICATIONS, and AIRBORNE IRRITANTS;

(j) the medical values of said categories of said second physical format consisting essentially of POLLENS, HOUSE DUST, MOLDS, PETS, MEDICATIONS, and AIRBORNE IRRITANTS;

(k) each of said queries in said first physical format being in contiguity with each of said categories of said first physical format;

(l) visual graphical elements preceding and emphasizing said queries within said categories of said first physical format;

(m) visual graphical elements succeeding and emphasizing said queries within said categories of said first physical format;

(n) said visual graphical elements being adapted for graphical selection;

(o) a series of actions in said second physical format in contiguity with each of said categories of said second physical format;

(p) visual graphical elements preceding and emphasizing said actions within said categories of said second physical format;

(q) visual graphical elements succeeding and emphasizing said actions within said categories of said second physical format;

(r) said visual graphical elements preceding and succeeding said actions and being adapted for graphical identification;

(s) said third physical format including at least one medicinal dosage specific to allergic rhinitis;

(t) removal of said dosages from said third physical format pursuant to said actions inherently establishing a usage that is related to said queries.

20. A medical system for treating allergic rhinitis, said medical package comprising:

(a) a combination of graphical indicia and medicinal dosages in at least a first physical format, a second physical format and a third physical format;

(b) said first physical format, in reference to a Step 1, including a record containing references to a plurality of categories that enable allergy assessment;

(c) said second physical format, in reference to a Step 2, including a record containing references to a plurality of categories that enable exposure reduction;

(d) said third physical format, in reference to a Step 3, including medicinal dosages adapted for allergic rhinitis;

(e) said first physical format, in reference to said Step 1, including a record that refers to a plurality of categories of interactive queries;

(f) each of said categories in said first physical format being designated by a query identifier that is unique within said Step 1;

(g) the query identifiers of said first physical format including POLLENS, HOUSE DUST, MOLDS, PETS, MEDICATIONS, and AIRBORNE IRRITANTS;

(h) a series of queries following each of said query identifiers;

(i) a check box at the beginning of each of said queries of said series of queries;

(j) a question mark at the end of each of said queries of said series;

(k) said check box and said question mark being adapted to facilitate identification of applicable queries;

(l) said second physical format, in reference to a Step 2, including a record that refers to a plurality of categories of interactive actions;

(m) each of said categories in said second physical format being designated by an action identifier that is unique within step 2;

(n) the action identifiers including POLLENS, HOUSE DUST, MOLDS, PETS, MEDICATIONS, and AIRBORNE IRRITANTS;

(o) a series of actions following each of said action identifiers;

(p) a visual attention symbol at the beginning of each of said actions of said series of actions;

(q) an exclamation mark at the end of each of said actions of said series of actions;

(r) said visual attention symbol and said exclamation mark being adapted to facilitate selection of a specific regimen of dosages;

(s) indicia in said third physical format that designate increments of time in proximity to said modules to establish a time line that is related to said query identifiers and said action identifiers;

(t) each query identifier of said first physical format in said Step 1 being in a first sequence;

(u) each action identifier of said second physical format in said step 2 being in a second sequence;

(v) said first sequence and said second sequence being substantially identical;

(w) removal of dosages pursuant to said selected queries and actions being adapted to inherently establish a permanent record of usage that is related to said queries and actions;

(x) whereby said queries of said first physical format in said Step 1 identify relevant allergenic substances and conditions, said actions of said second physical format in said Step 2 identify relevant needed actions, and said medication of said third physical format in said Step 3 provides comprehensive coordinated management of allergic disorders.

21. The medical system of claim 20 wherein said third physical format includes a multi-day medication regimen of a decongestant.

22. The medical system of claim 20 wherein said third physical format includes a multi-day medication of an antihistamine.

* * * * *